US009775555B2

(12) United States Patent
Pellegrini

(10) Patent No.: US 9,775,555 B2
(45) Date of Patent: *Oct. 3, 2017

(54) INTER-URETER SIGNALING DEVICE

(71) Applicant: Joanmarie Dietz Pellegrini, Holden, ME (US)

(72) Inventor: Joanmarie Dietz Pellegrini, Holden, ME (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/404,026

(22) Filed: Jan. 11, 2017

(65) Prior Publication Data

US 2017/0119299 A1    May 4, 2017

Related U.S. Application Data

(63) Continuation-in-part of application No. 14/715,391, filed on May 18, 2015, now Pat. No. 9,579,059.

(60) Provisional application No. 62/003,585, filed on May 28, 2014.

(51) Int. Cl.
*A61B 5/20*        (2006.01)
*A61B 5/00*        (2006.01)
*G08B 3/00*        (2006.01)
*G08B 5/36*        (2006.01)

(52) U.S. Cl.
CPC ............ *A61B 5/201* (2013.01); *A61B 5/6852* (2013.01); *A61B 5/746* (2013.01); *G08B 3/00* (2013.01); *G08B 5/36* (2013.01)

(58) Field of Classification Search
None
See application file for complete search history.

(56) References Cited

U.S. PATENT DOCUMENTS

| | | |
|---|---|---|
| 8,617,155 B2 | 12/2013 | Johnson et al. |
| 8,623,004 B2 | 1/2014 | Johnson et al. |
| 2006/0235458 A1 | 10/2006 | Belson |
| 2010/0004706 A1 | 1/2010 | Mokelke et al. |
| 2013/0030262 A1 | 1/2013 | Burnett et al. |
| 2013/0267777 A1 | 10/2013 | Avistan et al. |
| 2014/0058288 A1 | 2/2014 | Bartol et al. |

*Primary Examiner* — Devin Henson
*Assistant Examiner* — Benjamin Melhus
(74) *Attorney, Agent, or Firm* — Anthony D. Pellegrini

(57) ABSTRACT

An inter-ureter signaling device intended to provide a surgeon with a signal to identify when a ureter is grasped by a surgical clamping device, such as a pair of forceps, the device being comprised of a catheter, a signal generator, and wiring, such that when the catheter component of the device, having been inserted into a ureter, is compressed by the surgical clamping device an electrical circuit is closed and the signal generator generates a human perceptible signal, indicating that the clamp has been placed on the ureter.

14 Claims, 2 Drawing Sheets

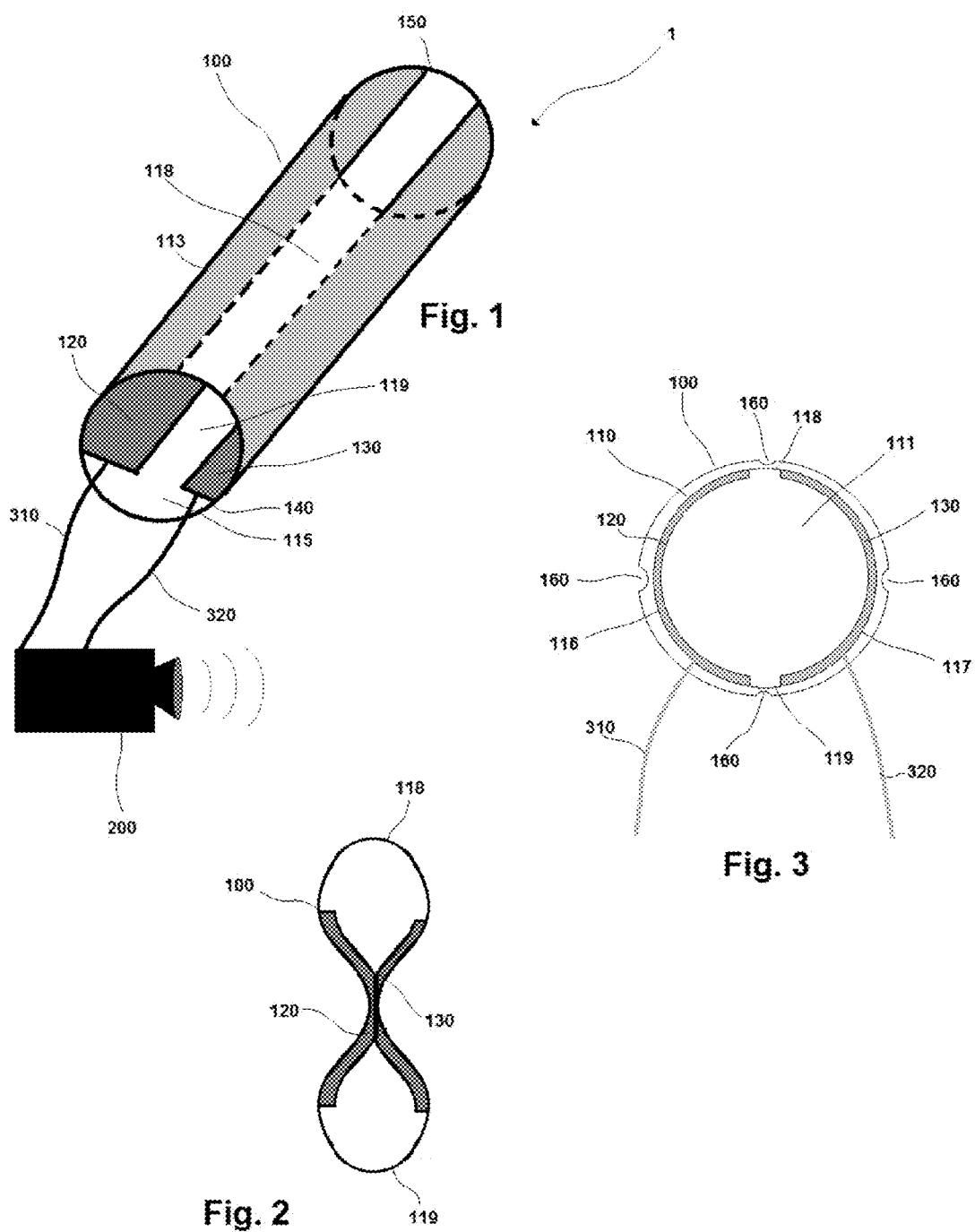

INTER-URETER SIGNALING DEVICE

CROSS REFERENCE TO RELATED APPLICATIONS

This application is a continuation in part of and claims priority to a pending patent application, U.S. Ser. No. 14/715,391, filed May 18, 2015, entitled Inter-Ureter Signaling Device, by Joanmarie D. Pellegrini, which is hereby incorporated by reference.

BACKGROUND

Surgeons operating on human patients often experience some difficulty in properly identifying tissue structures. If the wrong tissue structure is cut, the patient may suffer serious or even deadly consequences. This is a significant concern when surgery is performed proximate to the ureters. Because patients often have unique anatomy and because of the similarity in appearance of a ureter with other tissue structures, especially when viewed using laparoscopic instruments, inadvertent ureter dissections occur too frequently. What is therefore needed is a device that can easily and accurately alert the surgeon to the presence of a ureter, even when the ureter is not visually or otherwise identifiable by the surgeon.

SUMMARY

The device of the present invention is intended to provide a surgeon with a signal to identify when a ureter is grasped by a surgical clamping device, such as a pair of forceps. The device is comprised of a catheter, a signal generator, and wiring. The catheter component of the device contains at least two conducting members which together with the wiring comprise an electrical circuit suitable to enable operation of the signal generator. In one mode the conducting members of the catheter are separated from each other, resulting in an open circuit and thus preventing the signal generator from generating a signal. In another mode the conducting members of the catheter are in contact with each other, resulting in a closed circuit causing the signal generator to generate a signal.

To use the device, the catheter component is inserted into the ureter of a patient. The surgeon, prior to cutting any tissue structure proximate to the ureter, places a clamping device on the tissue structure intended to be cut. If the structure happens to be the ureter into which the catheter has been inserted, the pressure of the clamping device will cause the catheter to be compressed, thus bringing the conducting members into contact with each other, completing the electrical circuit and causing the signal generator to generate a signal perceptible to the surgeon, such as an audio tone. The surgeon, upon discerning the signal, is thus alerted to the fact that the structure being grasped by the clamping device is a ureter and can avoid cutting that structure.

In one embodiment, the catheter component is comprised of a single hollow tube, with the conducting members located on different portions of the inner surface of the tube. Compression of the catheter component brings the conducting members together. In this embodiment, the distal end of the catheter component is closed off, to prevent urine from entering the tube and potentially causing a short circuit. This embodiment may include longitudinal channels formed into the outer surface of the tube to permit urine to flow past the outer surface of the catheter.

In an alternate embodiment, the catheter component is comprised of a pair of hollow tubes, with the tubes having different diameters and the smaller diameter tube being placed within the larger diameter tube and spaced apart from the larger diameter tube by spacer elements. In this embodiment one of the conducting members is located along the inner surface of the larger diameter tube, and the other conducting member is located along the outer surface of the smaller diameter tube. Compression of the catheter component brings the conducting members together. The larger diameter outer tube is closed off at both ends, while the smaller diameter inner tube is open at both ends, with said open ends extending from the closed ends of the larger diameter outer tube, thus allowing urine to pass through the inner portion of the smaller diameter tube without coming into contact with the conducting members, avoiding a short circuit.

In yet another alternate embodiment, the catheter component is comprised of a pair of parallel hollow tubes, adjacent to each other and surrounded by a flexible outer sheath. One of the flexible hollow tubes is configured as described in the first embodiment, above, with its ends closed off, while the other flexible hollow tube is a standard ureteral catheter. Compression of the catheter component brings the conducting members together, as described above. This embodiment allows urine to pass through the inner portion of the second flexible hollow tube while preventing urine from coming into contact with the conducting members contained within the first flexible hollow tube, thus avoiding a short circuit.

DESCRIPTION OF THE DRAWINGS

FIG. 1 depicts a perspective view of one embodiment of the present invention, showing inner portions of the catheter in ghost lines.

FIG. 2 depicts a cross-sectional view of the embodiment of the present invention shown in FIG. 1 where the catheter is in its compressed state.

FIG. 3 depicts a cross-sectional view of the embodiment of the present invention shown in FIG. 1 where the catheter is in its uncompressed state.

DETAILED DESCRIPTION OF THE INVENTION

Figure 4:
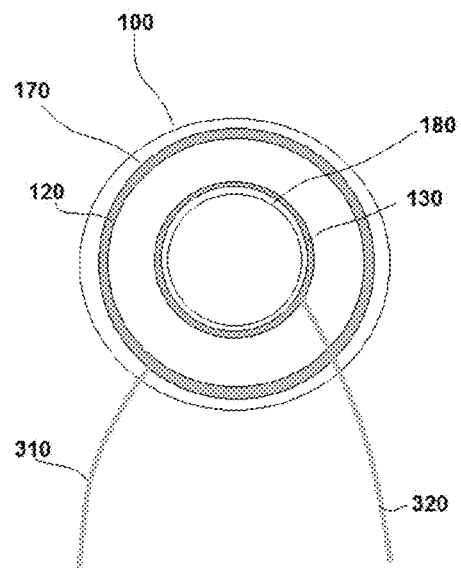
FIG. 4 depicts a cross-sectional view of an alternate embodiment of the present invention (spacers not shown).

The device 1 of the present invention comprises a catheter 100, a signal generator 200, and wiring 310, 320. See FIG. 1.

The catheter 100 must be suitably configured to be inserted into the ureter of a human subject. Its basic configuration is well known in the art, being a flexible hollow tube 110 with an outside diameter sufficiently small to fit within a ureter. The catheter 100 may be made of any suitable material known in the art, provided the material is non-conductive of an electrical charge. In the preferred embodiments the catheter 100 is made of silicone. Polyurethane is yet another alternative material for the catheter.

The flexible hollow tube 110 of the catheter 100 has an outer surface 113 and an inner surface 115, a proximate end 140 and a distal end 150, and defines an inner void 111.

The catheter 100 also comprises a first conducting member 120 and a second conducting member 130. The first and second conducting members 120, 130 may be made of any suitable material, provided they are flexible and capable of conducting an electrical charge. In the preferred embodiments the first and second conducting members 120, 130 are made of a thin layer of metallic material, such as copper foil.

The first and second conducting members 120, 130 are located along the inner surface 115 of the flexible hollow tube 110 of the catheter 100. The first conducting member 120 is located at a first portion 116 of the inner surface 115 of the flexible hollow tube 110 of the catheter 100, and the second conducting member 130 is located at a second portion 117 of the inner surface 115 of the flexible hollow tube 110 of the catheter 100. The first and second portions 116, 117 of the inner surface 115 of the flexible hollow tube 110 of the catheter 100 are separated by at least a third portion 118 of the inner surface 115 of the flexible hollow tube 110 of the catheter 100 and a fourth portion 119 of the inner surface 115 of the flexible hollow tube 110 of the catheter 100. That is, the first and second conducting members 120, 130 are not directly adjacent to each other. In a preferred embodiment, the first conducting member 120 is a thin ribbon arrayed in longitudinal orientation along the inner surface 115 of the flexible hollow tube 110 and the second conducting member 130 is a thin ribbon arrayed in longitudinal orientation along the inner surface 115 of the flexible hollow tube 110. The widths of the first and second conducting members 120,130 are each slightly less than fifty percent of the inner circumference of the flexible hollow tube 110, and the lengths of the first and second conducting members 120,130 are each substantially the same as the length of the flexible hollow tube 110. See FIG. 1. Other configurations of the first and second conducting members 120,130 are also contemplated by the present invention.

The catheter 100 has a compressed state and an uncompressed state. The compressed state of the catheter 100 is achieved when the flexible hollow tube 110 of the catheter 100 is distorted by external pressure exerted on the outer surface 113 of the flexible hollow tube 110, with the distortion being sufficient to cause portions of the inner surface 115 of the flexible hollow tube 110 of the catheter 100 to be brought into close proximity with each other resulting in at least a portion of the first conducting member 120 being brought into contact with at least a portion of the second conducting member 130. See FIG. 2. The uncompressed state of said catheter 100 is achieved when the first conducting member 120 is not in contact with the second conducting member 130. See FIG. 3. Even a partially compressed catheter 100 is deemed to be in its uncompressed state as long as the first conducting member 120 is not in contact with the second conducting member 120.

The signal generator 200 of the present invention is any device powered by an electrical current that is capable of generating a human perceivable signal. The signal may be audible, such as a musical tone or a buzzing noise or even a verbal prerecorded warning statement, or any other audible sound. The signal may be visual, such as a lamp. The signal may be a combination of audible and visual signals. The signal may be constant or intermittent. The signal generator 200 may be powered by alternating current or by direct current. It may use batteries, either rechargeable or disposable, as its power supply. The signal generator 200 may be integrated with one or more speakers, or visual display devices, or both. The signal generator 200 may be remotely in connection with one or more speakers, or visual display devices, or both, through wireless technology. These and other known configurations of the signal generator 200 are contemplated by the present invention.

The wiring component of the present invention must be capable of conducting an electrical current. The wiring connects the first and second conducting members 120,130 of the catheter 100 to the signal generator 200. The wiring has a first wire 310 and a second wire 320, with the first wire 310 being in connection with the first conducting member 120 and the signal generator 200 and the second wire 320 being in connection with the second conducting member 130 and the signal generator 200. The wiring can be made of any suitable material.

The wiring is configured as an open circuit when the first and second conducting members 120,130 of the catheter 100 are not in contact with each other and the wiring is configured as a closed circuit when the first and second conducting members 120,130 of the catheter 100 are in contact with each other. Thus, when the wiring is configured as the closed circuit an electrical current travels through the wiring causing the signal generator 200 to generate a human perceivable signal, and when the catheter 100 is configured as the open circuit the electrical current is interrupted by the separation between the first and second conducting members 120,130 of the catheter 100, thereby preventing the signal generator 200 from generating a human perceivable signal. As evident from the previous discussion, the open circuit configuration of the wiring is achieved when the catheter 100 is in its uncompressed state, and the closed circuit configuration of the wiring is achieved when the catheter 100 is in its compressed state.

In alternative embodiments of the present invention, there may be multiple first conducting members 120 and multiple second conducting members 130. Each of the multiple first conducting members 120 is separated from each of the multiple second conducting members 130 by portions of the inner surface 115 of the flexible hollow tube 110 of the catheter 100. Each of the multiple first conducting members 120 is further in connection with the first wire 310, and each of the multiple second conducting members 130 is further in connection with the second wire 320. When the catheter 100 is in its uncompressed state none of the multiple first conducting members 120 is in contact with any of the multiple second conducting members 130. When the catheter 100 is in its compressed state at least one of the multiple first conducting members 120 is in contact with at least one of the multiple second conducting members 130. In a preferred embodiment, the multiple first conducting members 120 are thin ribbons arrayed in longitudinal orientation along the inner surface 115 of the flexible hollow tube 110 and the multiple second conducting members 130 are thin ribbons arrayed in longitudinal orientation along the inner surface 115 of the flexible hollow tube 110, with the multiple first and second conducting members 120,130 alternating with each other so that between any two first conducting members 120 there is one second conducting member 130 and between any two second conducting members 130 there is one first conducting member 120. Other configurations, orientations, and numbers of first and second conducting members 120,130 are also contemplated by the present invention.

In the preferred embodiments of the present invention, the wiring enters the catheter 100 at the proximate end 140 of the flexible hollow tube 110, and the proximate end 140 and the distal end 150 of the flexible hollow tube 110 are closed off. This configuration of the catheter 100 prevents urine from entering the flexible hollow tube 110 and potentially causing a short circuit. This embodiment may also include one or more longitudinal channels 160 formed into the outer surface 113 of the flexible hollow tube 110 and running substantially the entire length of the flexible hollow tube 110, to permit urine to flow past the outer surface 113 of the catheter 100. See FIG. 3.

Figure 5:
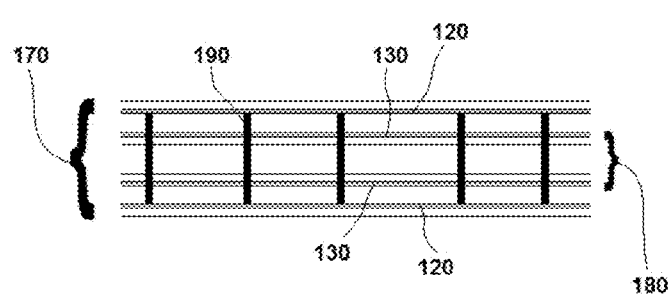
FIG. 5 depicts a cut-away side plan view of the embodiment of the present invention shown in FIG. 4.

In yet another embodiment of the present invention, the catheter 100 is comprised of a pair of concentrically aligned flexible hollow tubes 170,180. See FIG. 4. The flexible outer hollow tube 170 of the catheter 100 has an outer surface, an inner surface, and an inside diameter, and defines a first inner void 171. The flexible inner hollow tube 180 of the catheter 100 has an outer surface, an inner surface, and an outside diameter, and defines a second inner void 181. The outside diameter of the flexible inner hollow tube 180 of the catheter 100 is smaller than the inside diameter of the flexible outer hollow tube 170 of the catheter 100. The flexible inner hollow tube 180 of the catheter 100 is located within the first inner void 171, and is further located spaced apart from the flexible outer hollow tube 170 of the catheter 100. A plurality of spacers 190 keeps the flexible inner hollow tube 180 spaced apart from the flexible outer hollow tube 170, such that the outer surface of the flexible inner hollow tube 180 does not directly contact the inner surface of the flexible outer hollow tube 170. See FIG. 5. Each of the plurality of spacers 190 may be an annular ring, with each annular ring having an inner diameter and an outer diameter. The inner diameter of each said annular ring is substantially the same as the outer diameter of the flexible inner hollow tube 180 of the catheter 100, and the outer diameter of each said annular ring is substantially the same as the inner diameter of the flexible outer hollow tube 170 of the catheter 100. The spacers 190 are made of any suitable material, and should be flexible so that they compress when an external force is applied to the outer surface of the flexible outer hollow tube 170. They may be made of the same material as the flexible hollow tubes 170, 180. The spacers 190 should not be electrically conductive. The spacers 190 may be configured other than as annular rings, as long as they satisfy the requirement of keeping the flexible outer hollow tube 170 spaced apart from the flexible inner hollow tube 180 when the catheter 100 is in its uncompressed state.

Figure 6:
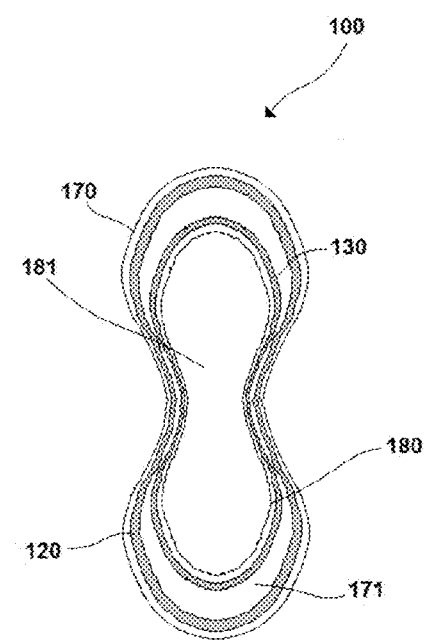
FIG. 6 depicts a cross-sectional view of the embodiment of the present invention shown in FIG. 4 where the catheter is in its compressed state.

In this embodiment, the first conducting member 120 is located along the inner surface of the flexible outer hollow tube 170 of the catheter 100 and the second conducting member 130 is located along the outer surface of the flexible inner hollow tube 180 of the catheter 100. The first conducting member 120 may completely cover the inner surface of the flexible outer hollow tube 170 of the catheter 100 or just a portion thereof. Similarly, the second conducting member 130 may completely cover the outer surface of the flexible inner hollow tube 180 of the catheter 100 or just a portion thereof. When the catheter 100 is in its compressed state, the inner surface of the flexible outer hollow tube 170 is placed in close proximity to the outer surface of the flexible inner hollow tube 180 such that at least a portion of the first conducting member 120 comes into contact with at least a portion of the second conducting member 130. See FIG. 6. The proximate and distal ends of the flexible outer hollow tube 170 are partially closed off, having apertures aligned with the proximate and the distal ends of the flexible inner hollow tube 180, which are both open. Urine may thus flow through the catheter 100 within the second inner void 181 without coming into contact with the first or second conducting members 120,130.

The present invention also discloses a method for identifying a ureter of a patient during surgery using the device disclosed above. This method comprises the following steps:

A. obtain an inter-ureter signaling device as described above;

B. insert said catheter of said inter-ureter signaling device into said ureter of said patient;

C. identify a tissue structure of said patient;

D. place a clamp onto said tissue structure;

E. observe whether a signal is generated by said inter-ureter signaling device; and F. make a determination as to whether the tissue structure is the ureter by performing one of the following two substeps:

F1. determine that the tissue structure that is clamped is the ureter if a signal is generated by said inter-ureter signaling device, or F2. determine that the tissue structure that is clamped is not the ureter if no signal is generated by said inter-ureter signaling device.

Modifications and variations can be made to the disclosed embodiments of the device 1 without departing from the subject or spirit of the invention as defined in the following claims.

I claim:

1. An inter-ureter signaling device comprising
a catheter,
a signal generator, and
wiring;
wherein said catheter being configured to be inserted into a ureter of a human subject,
said catheter being a first flexible hollow tube, with said first flexible hollow tube of said catheter having an outer surface and a hollow interior,
said catheter having a first conducting member and a second conducting member, with said first and second conducting members each being configured to independently conduct an electrical charge, whereby the first conducting member is located in the interior of the catheter and the second conducting member is located in the interior of the catheter spaced apart from the first conducting member, and
said catheter having a compressed state and an uncompressed state, with said compressed state of said catheter being achieved when the first flexible hollow tube of the catheter is distorted by external pressure on the outer surface of the first flexible hollow tube such that at least a portion of the first conducting member is brought into direct contact with at least a portion of the second conducting member whereby there is no structure interposed between said portion of the first conducting member and said portion of the second conducting member which are in direct contact with each other and there being no physical separation of said portion of the first conducting member and said portion of the second conducting member, and said uncompressed state of said catheter is achieved when the first conducting member is not in direct contact with the second conducting member whereby there is a physical separation between the first and second conducting members so that no electrical circuit is created between the first and second conducting members;
said signal generator being capable of generating a human perceivable signal; and
said wiring being capable of conducting an electrical current, wherein said wiring connects the first and second conducting members of the catheter to the signal generator, said wiring having a first wire and a second wire, with the first wire being in connection with the first conducting member and the signal generator and the second wire being in connection with the second conducting member and the signal generator;

whereby said wiring is configured as an open circuit when the first and second conducting members of the catheter are not in direct contact with each other and said wiring is configured as a closed circuit when at least a portion of the first conducting member of the catheter and at least a portion of the second conducting member of the catheter are in direct contact with each other, such that when the wiring is configured as the closed circuit an electrical current travels through the wiring causing the signal generator to generate a human perceivable signal, and when the wiring is configured as the open circuit the electrical current is interrupted by the physical separation between the first and second conducting members of the catheter thereby preventing the signal generator from generating a human perceivable signal.

2. The device of claim 1
wherein the first flexible hollow tube of the catheter has an inner surface,
whereby the first conducting member is located along the inner surface of the first flexible hollow tube of the catheter at a first portion of the inner surface of the first flexible hollow tube of the catheter in and the second conducting member is located along the inner surface of the first flexible hollow tube of the catheter at a second portion of the inner surface of the first flexible hollow tube of the catheter, whereby said first and second portions of the inner surface of the first flexible hollow tube of the catheter are separated by at least a third portion of the inner surface of the first flexible hollow tube of the catheter and a fourth portion of the inner surface of the first flexible hollow tube of the catheter.

3. The device of claim 2 wherein the catheter has a proximate end and a distal end,
with the wiring entering the catheter at said proximate end of the catheter and said distal end of the catheter being closed.

4. The device of claim 3 wherein the proximate end of the catheter is closed.

5. The device of claim 2 wherein the catheter has one or more longitudinal channels formed into the outer surface of the flexible hollow tube.

6. The device of claim 1 further comprising multiple first conducting members and multiple second conducting members,
with each of said multiple first conducting members being in connection with the first wire and with each of said multiple second conducting members being in connection with the second wire, and
with each of said multiple first conducting members being separated from each of said multiple second conducting members when the catheter is in the uncompressed state and with at least one of said multiple first conducting members being in contact with at least one of said multiple second conducting members when the catheter is in the compressed state.

7. The device of claim 1 wherein the signal generator is capable of generating an audible sound.

8. The device of claim 1 wherein the signal generator is capable of generating a visual signal.

9. The device of claim 1 wherein
the first flexible hollow tube of the catheter has an inner surface and an inside diameter,
the catheter further comprises a second flexible hollow tube, with said second flexible hollow tube of the catheter having an outer surface, a hollow interior, and an outside diameter, with the outside diameter of the second flexible hollow tube being smaller than the inside diameter of the first flexible hollow tube, said second flexible hollow tube of the catheter being located within the interior of the first flexible hollow tube, and said second flexible hollow tube of the catheter being located and spaced apart from the first flexible hollow tube of the catheter by a plurality of spacers, such that the outer surface of the second flexible hollow tube does not directly contact the inner surface of the first flexible hollow tube,
with the first conducting member located along the inner surface of the first flexible hollow tube of the catheter and the second conducting member located along the outer surface of the second flexible hollow tube of the catheter.

10. The device of claim 9 wherein each of the plurality of spacers is an annular ring, each said annular ring having an inner diameter and an outer diameter, with the inner diameter of each said annular ring the same as the outer diameter of the second flexible hollow tube of the catheter and the outer diameter of each said annular ring the same as the inner diameter of the first flexible hollow tube of the catheter.

11. The device of claim 9 wherein the proximate and distal ends of the first flexible hollow tube are partially closed off, having apertures aligned with the proximate and the distal ends of the second flexible hollow tube, which are both open.

12. A method for identifying a ureter of a patient during surgery, said method comprising the following steps:
A. obtain an inter-ureter signaling device,
said inter-ureter signaling device comprising
a catheter,
a signal generator, and
wiring;
wherein said catheter being configured to be inserted into a ureter of a human subject,
said catheter being a first flexible hollow tube, with said first flexible hollow tube of said catheter having an outer surface and a hollow interior,
said catheter having a first conducting member and a second conducting member, with said first and second conducting members each being configured to independently conduct an electrical charge, whereby the first conducting member is located in the interior of the catheter and the second conducting member is located in the interior of the catheter spaced apart from the first conducting member, and
said catheter having a compressed state and an uncompressed state, with said compressed state of said catheter being achieved when the first flexible hollow tube of the catheter is distorted by external pressure on the outer surface of the first flexible hollow tube such that at least a portion of the first conducting member is brought into direct contact with at least a portion of the second conducting member whereby there is no structure interposed between the portions of the first and second conducting members in direct contact with each other and no physical separation of said portions of the first and second conducting members, and said uncompressed state of said catheter is achieved when the first conducting member is not in direct contact with the second conducting member whereby there is a physical separation between the first and second conducting members so that no electrical circuit is created between the first and second conducting members;

said signal generator being capable of generating a human perceivable signal; and said wiring being capable of conducting an electrical current, wherein said wiring connects the first and second conducting members of the catheter to the signal generator, said wiring having a first wire and a second wire, with the first wire being in connection with the first conducting member and the signal generator and the second wire being in connection with the second conducting member and the signal generator, whereby said wiring is configured as an open circuit when the first and second conducting members of the catheter are not in direct contact with each other and said wiring is configured as a closed circuit when at least a portion of the first and second conducting members of the catheter are in contact with each other, such that when the wiring is configured as the closed circuit an electrical current travels through the wiring causing the signal generator to generate a human perceivable signal, and when the wiring is configured as the open circuit the electrical current is interrupted by the physical separation between the first and second conducting members of the catheter thereby preventing the signal generator from generating a human perceivable signal;

B. insert said catheter of said inter-ureter signaling device into said ureter of said patient;

C. identify a tissue structure of said patient;

D. place a clamp onto said tissue structure;

E. observe whether a signal is generated by said inter-ureter signaling device; and F. make a determination as to whether the tissue structure is the ureter by performing one of the following two Substeps:

F1. determine that the tissue structure that is clamped is the ureter if a signal is generated by said inter-ureter signaling device, or F2. determine that the tissue structure that is clamped is not the ureter if no signal is generated by said inter-ureter signaling device.

13. The method of claim 12 wherein the signal generator is capable of generating an audible sound.

14. The method of claim 12 wherein the signal generator is capable of generating a visual signal.

* * * * *